United States Patent [19]

Gay

[11] Patent Number: 4,628,027
[45] Date of Patent: Dec. 9, 1986

[54] VITRO DIAGNOSTIC METHODS USING MONOCLONAL ANTIBODIES AGAINST CONNECTIVE TISSUE PROTEINS

[75] Inventor: Steffen Gay, Birmingham, Ala.

[73] Assignees: Molecular Engineering Associates, Ltd.; The Board of Trustees of the Universtiy of Alabama, both of Birmingham, Ala.

[21] Appl. No.: 601,438

[22] Filed: Apr. 18, 1984

Related U.S. Application Data

[63] Continuation of Ser. No. 379,704, May 19, 1982, abandoned.

[51] Int. Cl.[4] .................. G01N 33/68; G01N 33/577
[52] U.S. Cl. ........................................ 435/7; 435/68;
435/172.2; 436/506; 436/538; 436/536; 436/540; 436/542; 436/548; 436/811; 436/813; 436/815; 424/85; 424/1.1
[58] Field of Search ............... 436/518, 527, 528–531, 436/536–540, 542, 548, 804, 811, 813, 815, 823, 436/824, 546; 435/4, 7, 28, 29, 68, 70, 172.2, 240, 435/948; 935/104, 107, 108, 110; 424/85, 11.1

[56] References Cited

U.S. PATENT DOCUMENTS

| | | | |
|---|---|---|---|
| 4,172,124 | 10/1979 | Koprowski et al. | 424/85 |
| 4,196,265 | 4/1980 | Koprowski et al. | 424/85 |
| 4,271,145 | 6/1981 | Wands et al. | 424/85 |
| 4,312,853 | 1/1982 | Timpl | 424/1.1 |
| 4,340,581 | 7/1982 | Timpl | 424/1.1 |
| 4,410,506 | 10/1983 | Price | 436/542 |
| 4,485,100 | 11/1984 | Hochstrasser | 424/177 |
| 4,504,587 | 3/1985 | Timpl | 436/539 |
| 4,565,789 | 1/1986 | Liotta | 436/504 |

FOREIGN PATENT DOCUMENTS

83/04104 11/1983 PCT Int'l Appl. .

OTHER PUBLICATIONS

Liotta, L. A. et al, The Lancet, Jul. 21, 1979, pp. 146–147.
Ristelli, J. et al, Fresenius Z. Anal. Chem. 301, 122 (1980).
Rennard, S. I. et al, Anal. Bioch., 104:205–214 (1980).
Ristelli, J. et al, Anal. Bioch., 113:372–378 (1981).
Gay, S. et al, VIIIth Southeastern Meeting, Amer. Rheum. Assoc., Abstr. 1 (1981).
Sundar Raj, N. et al, J. Cell Biology, vol. 91 (2):8027 (1981).
Linsennmayer, T. F. et al, Biochem. Biophys. Res. Comm., 92(2):440–446–(1980).
Linsenmayer, T. F. et al, Proc. Natl. Acad. Sci., USA, vol. 76(8), pp. 3703–3707 (1979).
Sundar Raj, N. et al, Biochem. Biophys. Res. Comm., 106(1), 48–57(1982), CA 97(1):44315.
Hollister, D. W. et al, Collagen Related Res.: Clin. Exp., 2(3), 197–210 (1982), CA97(19):160788u.
Sakai, L. Y. et al, Am. J. Pathol., 108(3), 310–318 (1982), CA97(21):179907d.
Sundar Raj, N. et al, Immunology, vol. 47 (1), pp. 133–140 (1982), CA97(23):196637h.
Foellmer, H. G. et al, Protides Biol. Fluids, 29th, 773–776, vol. Date 1981, (1982), CA97(7):51951w.
Stocker, S. et al, Dev. Immunol., 18, 85–90 (1983) CA100(5):(31649f).
Hessle, H. et al, J. Biol. Chem., 259(6):3955–3961 (1984).
Matsubara, T. et al, Exp. Cell. Biol., vol. 52(3), pp. 159–169 (1984), CA101(1):4430s.
Foellmer, H. G. et al, Lab. Invest., 48(5), 639–652 (1983), CA99(5):35413h.
Foellmer, H. G. et al, Eur. J. Biochem., vol. 134(1), 183–189 (1983), CA99(9):68669z.
Matsubara, T. et al, Exp. Cell. Biol., 52(1), 1–11 (1984), CA100(7):49130q.
Scheinman, J. I. et al, Lab. Invest., 50(1), 101–112 (1984), CA100(13):99259j.
Gay, S. and Miller, E. J., Collagen in the Physiology and Pathology of Connective Tissue (Gustav Fischer Verlag) New York (1978).
von der Mark, K., International Review of Connective Tissue Research, 9:265 (1981).
Foellmer, H. et al., Fed. Proc. (Abstr.) 40:794 (4–1981).
Scheinman, J. et al., Fed. Proc. (Abstr.) 41:616 (1982).
Foellmer, A. et al., Fed. Proc. (Abstr.) 41:616 (1982).
Walsh et al., Dev. Biol. 84:121 (1981).
Pierschbacher et al., Cell 26:259 (1981).
Oh et al., Proc. Natl. Acad. Sci. USA 78:3218 (1981).
Zardi et al., Int. J. Cancer 25:325 (1980).
Schoen et al., Hybridoma, 1:99 (1982).
Kuusela et al., Scand. J. Immunol. 12:331 (1980).
Linsenmayer et al., Anatomical Record 193:605 (1979).
Linsenmayer et al., J. Cell Biol. (Abstr.) 83:463a (1979).
Gay et al., Proc. Natl. Acad. Sci. USA 73:4037 (1976).
Gay et al., Collagen Rel. Res. 1:337 (1981).
Nowack et al., J. Immunol. Methods 12:117 (1976).
Reddi et al., Cell Biology 12:5589 (1977).
Gay et al., Coll. Res. 1:53 (1981).
Timpl et al., J. Immunol. Methods 18:165 (1977).
von der Mark et al., Dev. Biol. 48:237 (1976).

(List continued on next page.)

*Primary Examiner*—Charles F. Warren
*Assistant Examiner*—M. Moskowitz
*Attorney, Agent, or Firm*—Pennie & Edmonds

[57] ABSTRACT

Collagen profiles of human body tissues and fluids, i.e., the types of distinct connective tissue proteins present, their distribution in human body tissues and fluids, and the concentration ratios among distinct types, are subject to change during certain pathological conditions and during therapeutic regimens for the treatment of such conditions. These changes in collagen profiles can be detected by immunohistological, immunocytological and immunoserological techniques. In vitro diagnostic methods employing monoclonal antibodies specific for connective tissue proteins are provided which can be used for monitoring the results of therapeutic measures taken against inflammatory diseases, fibrotic diseases and cancer and for detecting or following the pathogenesis of such diseases.

60 Claims, No Drawings

OTHER PUBLICATIONS

Gay et al., Metab. Bone Dis. Rel. Res., 2:97 (1980).
Breitkreutz et al., Cancer Research, 39:5093 (1979).
Fleischmajer et al., J. Invest. Derm. 75:189 (1980).
Guzelian et al., Gastroenterology (Abstr.) 79:1024 (1980).
Gay et al., Klin, Wschr. 53:205 (1975).
Gay et al., Osteoarthritis Symposium (Grune & Stratton), 43 (1981).
Sauk et al., J. Oral Path. 9:210 (1980).
Gay et al., J. Cutaneous Path., 6:91 (1979).
Gay et al., Klin. Wschr., 53:899 (1975).
Claque et al., J. Immunol. Methods 27:31 (1979).
Rohde et al., J. Immunol. Methods 11:135 (1976).
Gosslau et al., J. Immunol. Methods 29:71 (1979).

VITRO DIAGNOSTIC METHODS USING MONOCLONAL ANTIBODIES AGAINST CONNECTIVE TISSUE PROTEINS

This is a continuation of application Ser. No. 379,704 filed May 19, 1982, now abandoned.

TABLE OF CONTENTS

1. Introduction
2. Background of the Invention
   2.1. Monoclonal Antibodies
   2.2. Connective Tissue Proteins
   2.3. Pathological Conditions Involving Connective Tissue Proteins
   2.4. Biochemical Approaches to the Study of Collagen and Connective Tissue Pathology
   2.5. Immunological Approaches to the Study of Collagen and Connective Tissue Pathology
3. Summary of the Invention
4. Description of the Invention
   4.1. The Antigens
   4.2. Somatic Cells
   4.3. Myeloma Cells
   4.4. Fusion
   4.5. Isolation of Clones and Antibody Detection
   4.6. Cell Propagation and Antibody Production
   4.7. In Vitro Diagnostic Uses for Monoclonal Antibodies to Connective Tissue Proteins
   4.8. Therapy Monitoring Using Monoclonal Antibodies Against Connective Tissue Proteins
   4.9. Analytical Methods
      4.9.1. Radioimmunoassay
      4.9.2. Enzyme-Linked Immunosorbent Assay
      4.9.3. Immunohistological and Immunocytological Staining
      4.9.4. Immunoelectronmicroscopy
5. Examples
   5.1. Construction of Hybridomas Secreting Monoclonal Antibodies to Connective Tissue Proteins
      5.1.1. Purification of Connective Tissue Proteins
      5.1.2. Immunization Schedules
      5.1.3. Spleen Cell Preparation
      5.1.4. Myeloma Cell Preparation
      5.1.5. Fusion Procedure
      5.1.6. Outgrowth and Selection
      5.1.7. Immunological Characterization of Hybrid-Produced Monoclonal Antibodies
      5.1.8. Cloning of Hybrids
      5.1.9. Stability of Phenotype Determination
      5.1.10. Determination of Monoclonal Antibody Specificity
      5.1.11. Propagation of Hybrid Cells and Antibody Production
   5.2. Detection and Measurement of Connective Tissue Proteins in Biological Fluids with Monoclonal Antobodies
      5.2.1. Radioimmunoassay
      5.2.2. Enzyme-Linked Immunosorbent Assay
   5.3. Immunohistological Application of Monoclonal Antibodies Against Connective Tissue Proteins
      5.3.1. Immunofluorescent Staining of Biopsied Tissue Sections
      5.3.2. Immunoelectronmicroscopy
   5.4. Immunocytological Application of Monoclonal Antibodies Against Connective Tissue Proteins

1. INTRODUCTION

This invention relates to the production of antibodies specific for connective tissue proteins and, more particularly, to the production of monoclonal antibodies by fused cell hybrids against human collagens and enzymes involved in collagen degradation. Collagen is by far the most prevalent human protein, constituting almost half of the total body proten. The prolific research in recent years in the area of collagen biochemistry has demonstrated that there are at least six genetically distinct collagens and several related collagen-degrading enzymes.

The collagen profile, i.e., the types of distinct collagens and collagen-associated proteins present, their distribution in the tissue, and the concentration ratios among the distinct types, of any given tissue or body fluid sample varies with the tissue or fluid source. Moreover, the collagen profile of a tissue or fluid sample also varies with the physiological or pathological state of its course. In fact, there are numerous connective tissue disorders and other pathological conditions in which changes in the collagen profile occur, eventually resulting in such large scale tissue alterations as to cause organ impairment. Hence, a specific and reliable means for detecting and/or quantitatively measuring changes in collagen types and distribution in tissue and body fluids is extremely useful for diagnostic evaluations of the stage of and specific organ involvement in certain diseases. Furthermore, the detection and/or quantitative measurement of different types of collagens and collagen-associated enzymes in body fluids provides a means for monitoring therapies that result in a release of collagens and collagen-associated enzymes into body fluids upon the eradication of cells, such as tumor cells, against which the drug is targeted.

The use of monoclonal antibodies against connective tissue proteins to establish the collagen profile of histological, cytological and biological fluid samples is a novel and advantageous approach to disease diagnosis and therapy monitoring. Because of the high specificity and sensitivity of monoclonal antibodies, early detection of certain collagen-related pathological conditions is possible as is early assessment of the efficacy of certain therapeutic programs. To achieve these goals, the invention provides: (1) a method for repeatedly producing large quantities of monospecific antibodies against distinct connective tissue proteins and (2) procedures for using the monoclonal antibodies individually or in combination as clinical probes for diagnosis and therapy monitoring. The potential prognostic importance of early and accurate disease diagnosis and determination of the usefulness of certain therapies using the methods of this invention is highly significant.

2. BACKGROUND OF THE INVENTION

2.1. MONOCLONAL ANTIBODIES

Kohler and Milstein are generally credited with having devised the technique that successfully resulted in the formation of the first monoclonal antibody-producing hybridomas [G. Kohler and C. Milstein, Nature 256: 495–497 (1975); Eur. J. Immunol. 6: 511–519 (1976)]. By fusing antibody-forming cells (spleen lymphocytes) with myeloma cells (malignant cells of bone marrow primary tumors) they created a hybrid cell line, arising from a single fused cell hybrid (called a hybridoma or clone) which had inherited certin characteristics of both the lymphocytes and myeloma cell lines. Like the lymphocytes (taken from animals primed with sheep red blood cells as antigen), the hybridomas secreted a single type of immunoglobulin specific to the antigen; moreover, like the myeloma cells, the hybrid cells had the potential for indefinite cell division. The combination of these two features offered distinct advantages over conventional antisera. Whereas antisera derived from vaccinated animals are variable mixtures of polyclonal antibodies which never can be reproduced identically, monoclonal antibodies are highly specific immunoglobulins of a single type. The single type of immunoglobulin secreted by a hybridoma is specific to one and only one antigenic determinant on the antigen, a complex molecule having a multiplicity of antigenic determinants. For instance, if the antigen is a protein, an antigenic determinant may be one of the many peptide sequences [generally 6–7 amino acids in length (M. Z. Atassi, Molec, Cell. Biochem. 32: 21–43 (1980)] within the entire protein molecule. Hence, monoclonal antibodies raised against a single antigen may be distinct from each other depending on the determinant that induced their formation; but for any given clone, all of the antibodies it produces are identical. Furthermore, the hybridoma cell line can be reproduced indefinitely, is easily propagated in vitro or in vivo, and yields monoclonal antibodies in extremely high concentration.

Monoclonal methods are generally applicable and have been used to produce antibodies to antigens other than the sheep red blood cells used by Kohler and Milstein. For instance, it has been reported that monoclonal antibodies have been raised against tumor cells [U.S. Pat. No. 4,172,124] and viruses [U.S. Pat. No. 4,196,265]. The production of monoclonal antibodies against certain collagens, procollagens (natural precursors of collagens) and a collagen-associated glycoprotein has also been reported. Linsenmayer et al. reported using the cell hybridization technique to produce monoclonal antibodies against chick Type I collagen [Proc. Natl. Acad. Sci. U.S.A. 76(8): 3703–3707 (1979)]; Linsenmayer and Hendrix later reported having produced a monoclonal antibody specific for chick Type II collagen [Biochem. Biophys. Res. Commun. 92: 440–446 (1980)]. Both antibodies have been used for biochemical and cytological studies of extracellular matrices involved in the morphogenesis of the embryonic chick. Walsh et al. [Dev. Biol. 84: 121–132 (1981)] have reported producing a monoclonal antibody against human fibronectin, a collagen-associated glycoprotein, as part of an investigation to define human muscle surface antigens. The biochemical and immunological characterization of monoclonal antibodies specific for human collagens, Types I, III and IV, and human procollagens Types I and III has recently been reported [N. Sundar-Raj et al., J. Cell Biol. (Abstr.) 91(2): 8027 (1981)]. Finally, a monoclonal antibody against the collagen degrading enzyme elastase has been used to study the pathogenesis of inflammatory joint disease [S. Gay et al., VIIIth Southeastern Meeting, Amer. Rheum. Assoc., Abstr. 1, (1981)].

2.2. CONNECTIVE TISSUE PROTEINS

Information on the biochemistry of the genetically-distinct collagent types and their role in biological processes has grown prolifically in recent years [P. Bronstein and H. Sage, Ann. Rev. Biochem. 49: 957–1003 (1980); S. Gay and E. Miller, Collagen in the physiology and pathology of connective tissue, Gustav Fischer Verlag, New York (1978)]. Currently, the known collagens can be subdivided into four categories based on their histological distribution [S. Gay et al., Arthritis and Rheumatism 23(8): 937–941 (1980)]. Each type of collagen has as its biosynthetic precursor a procollagen molecule which differs from the mature collagen molecule insofar as it has additional amino acid sequences at the amino and carboxy termini of each chain that are eventually cleaved by specific processing enzymes.

The interstitial collagen molecules comprise the majority of all the connective tissue proteins and account for nearly all fibrillar tissue components. This class of collagens represents four distinct molecular species: (1) the Type I collagen molecule which exhibits the chain composition $[\alpha 1(I)]2 \ \alpha 2(I)$. Fibers derived from Type I collagen are found throughout the entire organism primarily in supporting tissues which normally exhibit very little distensibility under physical stress: (2) the Type I-trimer collagen molecule which is comprised of three identical $\alpha 1(I)$ chains. This molecule has been described in certain chondrocyte cultures and other experimental systems, but its existence in normal tissue has not been firmly established; (3) the Type II collagen molecule which contains three $\alpha 1(II)$ chains. In most instances this species forms relatively thin fibrils and displays a tissue distribution restricted predominantly to cartilaginous structures such as articular cartilage and nucleus pulposus and to certain parts of the embryonic eye; and (4) the Type III collagen molecule which is composed of three $\alpha 1(III)$ chains. The fibrils formed by these molecules are usually found in a reticular network. The latter meshwork apparently contains in addition to Type III molecules certain quantities of a form of Type III procollagen indicating that the conversion of Type III procollagen to Type III collagen is incomplete. These procollagen molecules participate in the formation of fine non-striated filaments which are associated with the Type III fibrils.

The basement membrane collagens include at least two distinct collagen chains, the $\alpha 1(IV)$ and $\alpha 2(IV)$, which exhibit unique compositional features. The configuration of these chains within native collagen molecules is presently unknown. These collagens appear to be universally distributed as components of the morphologically distinct epithelial and endothelial basement membranes.

The pericellular collagens commonly referred to as Type V collagen contain three distinct chains, $\alpha 1(V)$, $\alpha 2(V)$ and $\alpha 3(V)$, which combine to form a variety of molecular species. Histologically, they are more predominant in cells derived from the vascular system as compared to other tissues and appear to form a pericellular exocytoskeleton.

In certain tissues there are high molecular weight aggregates which upon disulfide bond reduction and denaturation are found to contain unique collagenous subunits (Type VI collagen). These aggregates may serve as structural polypeptides linking collagenous sequences with noncollagenous sequences [D. Furuto and E. Miller, J. Biol. Chem. 255(1): 290–295 (1980); D. Furuto and E. Miller, Biochem. 20: 1635–1640 (1981)].

In addition to the various types of collagens, at least four collagen-associated glycoproteins also have been identified and characterized. Fibronectin is a glycoprotein produced by many cell types, e.g., fibroblasts, and is present on cell surfaces in an insoluble form. There is also a soluble form of fibronectin present in serum which is involved in blood coagulation. Apparently, fibronectin mediates the adhesion of cells to the extracellular collagen matrix [E. Ruoslahti et al., Coll. Res. 1: 95-128 (1981)]. Chondronectin, distinct from fibronectin in that it does not stimulate the attachment of fibroblasts to collagen, is produced by chondrocytes. It appears to be a chondrocyte-specific attachment protein, enhancing the attachment of chondrocytes to the collagenous matrix of cartilage [A. T. Hewitt et al., Proc. Natl. Acad. Sci. U.S.A. 77(1): 385-388 (1980)]. Osteonectin, another collagen-associated glycoprotein, also appears to be a tissue-specific protein, linking bone mineral and collagen phases. It may also initiate active mineralization in normal skeletal tissue [J. D. Termine et al., Cell 26: 99-105 (1981)]. Finally, laminin is a glycoprotein extractable from basement membranes which are ubiquitous structures of the body separating endothelial linings from underlying connective tissue in vessel walls. [H. Rohde et al., Hoppe-Seyler's Z. Physiol. Chem. 361: 1651-1660 (1980); J. Risteli et al., Fresenius Z. Anal. Chem. 301: 122 (1980)].

Several enzymes are involved in collagen biosynthesis and degradation and some have been better characterized than others [S. Gay and E. Miller, Collagen in the physiology and pathology of connective tissue, Gustav Fischer Verlag, New York (1978)]. Specific prolyl and lysyl hydroxylases convert the proline and lysine residues of procollagen chains to 3- and 4-hydroxyproline and hydroxylysine, respectively. The hydroxylysine residues may be further converted by galactosyl and glucosyl transferases to galactosylhydroxylysine and glucosylgalactosylhydroxylysine residues. After hydroxylation and glycosylation, three procollagen chains combine in a triple helix to form the procollagen molecule which is further processed by specific procollagen peptidases into the mature collagen molecule. In a final processing step, collagen molecules align to form fibrils which are cross-linked at terminal lysyl and hydroxylysyl residues by lysyl oxidase. Procollagens and cross-linked collagen molecules are susceptible to attack by specific collagen-degrading enzymes collectively called collagenases; cleavage by such enzymes yields procollagen peptides and collagen peptides. For instance, elastase is a very distinct collagen-degrading enzyme which selectively cleaves Type III collagen, but not Type I collagen, and releases a distinct trimer peptide, $\alpha 1(III)^B$. [C. Mainardi et al. J. Biol. Chem. 255(24): 12,006-12,010 (1980)].

2.3 PATHOLOGICAL CONDITIONS INVOLVING CONNECTIVE TISSUE PROTEINS

Pathological conditions involving connective tissue proteins are numerous and can be grouped roughly into three categories: conditions resulting from overt trauma, heritable disorders, and disorders commonly called acquired diseases. The pathophysiology of connective tissue that is characteristic of these disorders has been reviewed by Gay and Miller [S. Gay and E. Miller, Collagen in the physiology and pathology of connective tissue, Gustav Fischer Verlag, New York (1978). The conditions resulting from overt trauma lead to the initiation and progression of a variety of healing processes which may or may not result in full restoration of the injured tissues (e.g., skin, tendon or bone). The heritable disorders involve genetic defects or deficiencies in the formation of normal connective tissues. For instance, in Ehlers-Danlos syndrome IV, one the the important aspects of the pathophysiology of the disease appears to be a defect or deficiency in the synthesis and/or deposition of Type III collagen. Thus, the skin, blood vessels and intenstines, which normally contain relatively large amounts of collagen fibers derived from Type III molecules, are the tissues in which the clinical manifestations (spontaneous rupture of lage arteries and intestines and extensive ecchymoses resulting from minor traumas) appear most prominently.

Of the three categories of connective tissue pathology, it is in the acquired connective tissue disorders that changes in the collagen profile of afflicted tissues most notably occur as the disease progresses. The acquired disorders are pathophysiological conditions in which large scale tissue alterations occur as the result of an apparent lack of coordination between collagen synthesis and degradation. The disorders include atherosclerosis, liver cirrhosis, lung fibrosis, bone marrow fibrosis, systemic progressive sclerosis, sleroderma, psoriasis, rheumatoid arthritis, osteoarthrosis and certain benign and malignant tumors. For the most part, these conditions arise through fibroproliferative responses leading to an excessive accumulation of collagen in affected tissues though some disorders involve degenerative changes within previously normal connective tissues.

The patterns of collagen deposition in three different fibroproliferative disorders, atherosclerosis, liver fibrosis (or cirrhosis) and scleroderma of skin are quite similar and are illustrative of the types of changes in collagen profile that occur in the acquired connective tissue diseases. In the early stage of such pathological conditions, an increase in basement membrane collagen synthesis is first observed. The deposition of basement membrane matrix containing Type IV collagen is followed by a Type III collagen neosynthesis. The Type III collagen thereby forms the reticular network of granulation tissue. Finally the dense collagen fiber forms the scar tissue which is almost completely comprised of Type I collagen molecules [S. Gay, Ital. J. Gactroenterol. 12: 30-32 (1980)].

A number of tumors such as the various kinds of fibromatoses elaborate matrices containing copious quantities of fibrous collagen. Malignant tumors such as the osteosarcomas or chondrosarcomas may also produce large amounts of collagenous matrix. In these disorders, the collagen produced generally reflects the cellular origin of the tumor. Thus, osteosarcoma cells produce a matrix containing fibers derived from Type I molecules, whereas the fibrous elements of chondrosarcomas are derived from Type II molecules, [K. Remberger and S. Gay, Z. Krebsforsch. 90: 95-106 (1977)]. However, it is possible that less differentiated tumors may synthesize a number of different collagens. For instance, metastasized neoplastic mammary epithelial cells of breast carcinomas retain the ability to synthesize Type IV (basement membrane) collagen [L. A. Liotta et al., The Lancet, July 21, 1979: 146-147].

Rheumatoid arthritis is an acquired disease manifested by either fibroproliferative or degenerative changes in the connective tissue of diarthrodial joints. In the inflammatory-proliferative phase, rheumatoid synovial tissue is characterized by the synthesis and deposition of additional Type I and III collagens. The blood vessels of the proliferating pannus tissue carry the bulk of vascular-derived Type V collagen. The endothelial basement membrane containing Type IV collagen often appears irregular, discontinuous, and sometimes multilamellated in the vessels of pannus tissue. The altered basement membrane barrier is reflected by the cellular synovial exudate. The exudate contains phagocytes that exhibit inclusions of various collagens. The presence of different collagens in phagocytes of the synovial fluid is apparently due to degradation and erosion of different parts of the joint due to proteolytic activity on the part of collagenases. Phagocytosis of the vessel-derived collagens such as Type IV collagen from endothelium as well as Type V collagen surrounding smooth muscle cells and pericytes may reflect at least in part the degree of vascular necrosis. The presence of Type I and III collagen within the exudate cells suggests the destruction of the synovial matrix. However, the demonstration of considerable amounts of Type III collagen may also reflect collagen neosynthesis as observed in other fibro-proliferative disorders. The existence of Type II collagen in the snyovial phagocytes undoubtedly indicates the erosion of articular cartilage. From this discussion it is clear that the collagen profile of synovial exudate cells and synovial fluid can reflect the nature and extent of initial joint damage and the progress of the joint disease [S. Gay et al., Arthritis and Rheumatism 23(8): 937–941 (1980)].

Osteoarthrosis is an example of a noninflammatory joint disorder that involves degenerative loss of the articular cartilage. During the early stages of osteoarthrosis, articular cartilage is characterized by a loss of proteoglycan aggregates, presumably due to the release of unusually large amounts of degradative enzymes, which results in demasking Type II collagen fibers on fibrillated surfaces [S. Gay and R. K. Rhodes, Osteoarthritis Symposium, pp. 43–44, Grune & Stratton, Inc. (1981)]. In general, the fibrillated surface persists and the initial clefts eventually extend into the deeper layers of articular cartilage due to the inefficient healing and repair capacity of cartilage tissue. Chondrocytes do proliferate and form clusters adjacent to the cartilage clefts. Although these chondrocytes apparently retain their capacity to form new proteoglycan aggregates, the capacity to synthesize new cartilage specific Type II collagen molecules appears to be greatly diminished or lost. Instead, a small deposition of fibrocartilaginous material comprised of collagen fibers derived from Type I molecules occurs. The switch from Type II collagen synthesis to Type I collagen synthesis appears to be an important step in the pathogenesis of osteoarthrosis and hence the presence of Type I collagen in biopsies can serve as an indicator of the progress of the disease.

2.4 BIOCHEMICAL APPROACHES TO THE STUDY OF COLLAGEN AND CONNECTIVE TISSUE PATHOLOGY

Investigations on collagen in pathological states have frequently taken the form of: solubility (extractability) determinations in an effort to discern the state or extent of cross-linking; analyses of tissue hydroxyproline content as a measure of total collagen content; and evaluations of the capacity for collagen synthesis based on specific activity determinations in both in vivo and in vitro labeling experiments. Each of these approaches is inherently limited and therefore has several disadvantages. Thus the solubility or extractability of the collagen in a given specimen is heavily dependent on the physical state of the specimen, is often quite low, and most probably reflects the nature rather than the extent of the collagen cross-links prevalent within the tissue. Also, hydroxyproline determinations may provide misleading values for total collagen content due to the presence of other hydroxyproline-containing proteins such as elastin or Clq, as well as the presence of varying proportions of the various collagens. With respect to the latter point, the Type III collagen molecule contains about 30% more hydroxyproline than the Type I collagen molecule. Therefore, the total collagen content of a given specimen cannot be related to hydroxyproline content unless a reasonably accurate estimate of the proportions of these collagens in the tissue is available. And finally, the in vivo as well as in vitro labeling experiments are often difficult to interpret since rates of collagen degradation and pool sizes are not commonly evaluated. At best, then, these biochemical approaches provide only limited insight into the possible alterations in collagen chemistry and biosynthesis in diseased tissues. Moreover, they offer virtually no information with respect to the prevalence or disposition of the various collagens in such tissues, and hence are of limited or no diagnostic use.

2.5 IMMUNOLOGICAL APPROACHES TO THE STUDY OF COLLAGEN AND CONNECTIVE TISSUE PATHOLOGY

Even though the genetically distinct types of collagens are very similar to one another in their macromolecular structure, they are sufficiently different in their amino acid sequence to allow the production of specific antibodies. Antibodies can be raised against antigenic determinants located in five identifiable regions of collagen or procollagen molecules, specifically, the globular amino and carboxy termini of procollagen molecules, the non-helical termini of mature collagen molecules, the helical portion of collagen and procollagen molecules, and the central amino acid sequences of individual α-chains, obtained by denaturing collagen molecules. Thus, the antigenic regions in collagen consist both of sequential and conformational determinants.

Despite the weak antigenicity of collagen molecules, antibodies (in conventional antisera) have been successfully raised against distinct collagens, procollagens and collagen-associated proteins [Timpl et al., J. Immunol. Methods 18: 165–182 (1977), U.S. Pat. No. 4,312,853; J. Risteli et al., Fresenius Z. Anal. Chem. 301:122 (1980)] and have proved to be exceedingly useful reagents in elucidating the precise distribution of the various collagens in tissues and body fluids as well as in determining the capacity of certain cells to synthesize the various collagens. In fact, the information on the changes in collagen profiles which occurs during the connective tissue disorders discussed in Section 2.3 was obtained primarily through the use of immunohistological techniques and radioimmunoassays based on antibodies to the genetically distinct collagens.

While antibodies against collagens have been used mostly in connection with biological and biomedical research, the use of antibodies has also been suggested as a means for early clinical recognition of certain collagen-related diseases and other pathological conditions. A radioimmunoassay for Type III procollagen and Type III procollagen peptide has been reported by Timpl for the purpose of measuring these antigens in blood. Detection may indicate the presence of such possible disease states as liver cirrhosis or hepatitis [U.S. Pat. No. 4,312,853], which, at early stages, are often accompanied by the release of procollagen and procollagen peptide Type III into the serum and other body fluids. An immunohistochemical method for detecting Type IV (basement membrane) collagen-producing cells was reportedly used for the localization of single metastatic cells (which produce Type IV collagen and which could not be detected otherwise) in sections of lymph-nodes of breast cancer patients [L. A. Liotta et al., The Lancet, July 21, 1979: 146]. Radioimmunoassays for two basement membrane proteins, 7S collagen (non-Type IV) and the non-collagenous protein laminin have been reported by J. Risteli et al. [Fresenius Z. Anal. Chem. 301:122 (1980)]. The proposed use was for monitoring basement membrane disorders (such as the microangiopathic lesions of diabetes mellitus) by measuring the amount of these proteins circulating in the human blood stream. Enzyme-linked immunadsorbe assays have been developed for Types I, II, III, and IV collagen and for laminin and fibronectin by using antibodies prepared in rabbits and goats [S. I. Remnard et al., Anal. Biochem. 104: 205–214 (1980)].

Notably, all the antibodies used to detect the presence of collagens and collagen-associated proteins in body fluids and tissues and to study collagen distribution during pathological states have been polyclonal antibodies produced by conventional means. In other words, animals were immunized with highly purified preparations of connective tissue protein as antigen and their sera were harvested for use as antisera. Since various levels of cross-reacting antibodies may occur in the antisera, the specificity of such antisera must be increased by time-consuming immuno-adsorption procedures. This involves the passage of antisera to one type of collagen through a series of other collagen-containing columns to adsorb out antibodies that cross-react with the types of collagens distinct from the one used to raise the desired antibody. [Timpl et al., J. Immunol. Methods 18: 165–182 (1977)]. These procedures are capable of lowering the level of cross-reaction against other types of collagen to less than 0.1–1.0% of the total.

Adaptation of monoclonal techniques to the production of highly specific antibodies against the genetically distinct collagens and other connective tissue proteins for use in in vitro diagnostics and chemotherapy monitoring represents a clear improvement over previous immunological approaches to the detection of collagen-related pathological conditions. The fused cell hybrids made with these methods produce a single kind of antibody specific for the collagen antigen of interest. Higher titers of identical immunoglobulins are available in essentially limitless supply since the antibody-producing hybridomas can be cultured indefinitely in vitro or propagated in mice or other laboratory animals. Conventional methods for producing antibodies result in preparations of less specific polyclonal antisera which have to be purified extensively prior to use and can never be reproduced identically. The monoclonal approach, however, permits the quantitatively large-scale yet inexpensive production of highly specific antibodies, requiring minimal purification, if any, in small-scale culture vessels or laboratory animals.

3. SUMMARY OF THE INVENTION

Prior to the present invention, applicant believes there has been no report of a clinically useful preparation of monoclonal antibodies specific for all the known genetically distinct types of human collagens, collagen-associated enzymes and collagen peptide fragments resulting from enzymatic cleavage. Because collagen profiles of human body tissues and fluids change during certain pathological conditions and during therapeutic regimens and because the changes can be detected by immunohistological and immunoserological techniques, the monoclonal antibodies of this invention represent a new in vitro means of early and accurate disease or cancer diagnosis and monitoring of drug therapy.

The present invention provides a method for producing monoclonal antibodies against human collagens Types I through VI, the collagen degrading enzyme elastase and the $\alpha 1(III)^B$ peptide cleaved from Type III collagen by elastase. The monoclonal antibodies may be used in standard radioimmunoassays or enzyme-linked immunosorbent assays for the quantitative measurement of the spectrum of connective tissue proteins in a given sample of body fluid, thereby permitting non-invasive diagnosis of certain pathologocal states and the monitoring of therapies that result in release of connective tissue proteins into sera and other biological fluids. The monoclonal antibodies may be tagged with compounds which fluoresce at various wavelengths so that the distribution of collagens in tissue biopsies can be determined by immunohistological techniques. Radioimmunoassays and immunohistological methods employing the monoclonal antibodies of this invention can be used to detect and follow the pathogenesis of diseases, such as: genetic disorders affecting skeleton, skin and muscles; formation of excessive scar tissue; and deposition of pathological amounts of connective tissue in body organs, including kidney, intestines and heart, and in liver by liver cirrhosis, in skin by scleroderma; in lung by lung fibrosis; in bone marrow by leukemia; in blood vessels by atherosclerosis; and in joints by rheumatic diseases. The methods involving monoclonal antibodies can also be used to detect changes in the neosynthesis of collagens that is indicative or suggestive of the malignant state of cells derived from such tumors as breast carcinomas.

Because the monoclonal antibodies are produced by hybridoma techniques, the present invention provides theoretically immortal cell lines capable of consistently producing high titers of single specific antibodies against the distinct connective tissue proteins. This is a distinct advantage over the traditional technique of raising antibodies in immunized animals where the resulting sera contain multiple antibodies of different specificities that vary in both type and titer with each animal, and, in individual animals, with each immunization.

The invention contemplates the extension of the hybridoma technique to the production of monoclonal antibodies to other genetically distinct collagens and collagen-associated proteins and enzymes as they become known and their use in the in vitro diagnosis of disorders and cancers involving connective tissue proteins.

The invention further contemplates the use of monoclonal or polyclonal antibodies against connective tissue proteins for in vivo diagnostic and therapeutic purposes. Antibodies produced by either conventional methods or the monoclonal techniques of this invention can be labelled with radioactive compounds, for instance, radioactive iodine, and administered to the patient. The antibodies localize in areas of active collagen neosynthesis such as certain malignant tumors or other tissues undergoing pathological changes involving collagen. The localization of the antibodies can then be detected by emission tomographical and radionuclear scanning techniques; such detection is of diagnostic value. In addition, monoclonal or polyclonal antibodies against connective tissue proteins can be conjugated to certain cytotoxic compounds (radioactive compounds or other therapeutic agents) and can be used for therapeutic purposes, for instance, cancer therapy. The antibodies, targeted for malignant cells expressing the appropriate collagen antigen, localize on or in the vicinity of the individual cells or tumor at which point the conjugated cytotoxic compound takes effect to eradicate the malignant cells.

4. DESCRIPTION OF THE INVENTION

4.1. THE ANTIGENS

The genetically distinct types of collagens and other connective tissue proteins can be derived from a variety of tissue sources throughout the human body. For instance, Type I collagen is found in virtually all major connective tissues (bone, tendon and dentin) and in the stroma of several organs. It is present in dermis, vessel walls, the uterine wall and fibrocartilages. Type II collagen is most conveniently isolated from extracts of hyaline cartilage from joints; it can be found in respiratory passages and also comprises most of the fetal skeleton. Type III collagen may be isolated from dermis, vessel walls or the uterine wall and can be separated from Type I collagen molecules by differential salt precipitation. Type III collagen may also be derived from fetal tissues which are also a source of Type III procollagen. Type IV or basement membrane collagens may be conveniently isolated from the lens capsule or glomeruli of kidney tissue. Vascular tissues are a source of Type V collagen while Type VI collagen may be isolated from human placenta. Purification of the collagens has been described in the literature [E. Miller and R. Rhodes, Structural and contractile proteins, in: L. Cunningham and D. Frederiksen (editors), Methods in Enzymology, Academic Press, New York (1981)].

Depending on the antibody desired, any one of these distinct connective tissue proteins is a suitable antigen with which to prime animals, such as mice or rabbits, to obtain antibody-producing somatic cells for fusion. In other words, animals can be immunized against the antigen by administering an injection or series of injections (an initial shot and one or more boosters) of the connective tissue protein over the course of several weeks before taking the antibody-producing somatic cells from the animals. The choice of animal can influence the type of antibody obtained vis a vis the determinant on the antigen against which the antibody is directed. For example, if antibodies directed toward amino or carboxy terminal determinants are desired, rabbits should be immunized. When rats or mice are immunized, antibodies produced against determinants in the more stable helical portion of the various collagen molecules are usually the result.

4.2. SOMATIC CELLS

Somatic cells with the potential for producing antibody and, in particular, B cells, are suitable for fusion with a B-cell myeloma line. Those antibody-producing cells that are in the dividing plasmablast stage fuse preferentially. Somatic cells may be derived from the lymph nodes and spleens of primed animals and the lymphatic cells of choice depends to a large extent on their empirical usefulness in the particular fusion system. Once-primed or hyperimmunized animals can be used as a source of antibody-producing lymphocytes. Mouse lymphocytes give a higher percentage of stable fusions with the mouse myeloma lines described in Section 4.3. However, the use of rabbit, human and frog cells is also possible.

4.3. MYELOMA CELLS

Specialized myeloma cell lines have been developed from lymphocyte tumors for use in hybridoma-producing fusion procedures [G. Kohler and C. Milstein, Europ. J. Immunol. 6: 511–519 )1976); M. Shulman et al., Nature 276: 269–270 (1978)]. The cell lines have been developed for at least three reasons. The first is to facilitate the selection of fused hybridomas among unfused and similarly indefinitely self-propogating myeloma cells. Usually, this is accomplished by using myelomas with enzyme deficiencies that render them incapable of growing in certain selective media that support the growth of hybridomas. The second reason arises from the inherent ability of lymphocyte tumor cells to produce their own antibodies. The purpose of using monoclonal techniques is to obtain immortal fused hybrid cell lines that produce the desired single specific antibody genetically directed by the somatic cell component of the hybridoma. To eliminate the production of tumor cell antibodies by the hybridomas, myeloma cell lines incapable of producing light or heavy immunoglobulin chains or those deficient in antibody secretion mechanisms are used. A third reason for selection of these cell lines is for their suitability and efficiency for fusion.

Several myeloma cell lines may be used for the production of fused cell hybrids, including X63-Ag8 NSI-Ag4/1, MPC11-45.6TG1.7, X63-Ag8.653, Sp2/0-Ag14, FO, and S194/5XXO.BU.1, all derived from mice, 210.RCY3.Ag1.2.3 derived from rats and U-226AR and GM1500GTGAL$_2$, derived from humans. [G. J. Hammerling, U. Hammerling and J. F. Kearney (editors), Monoclonal antibodies and T-cell hybridomas in: J. L. Turk (editor) Research Monographs in Immunology, Vol. 3, Elsevier/North Holland Biomedical Press, New York (1981)].

4.4 FUSION

Methods for generating hybrids of antibody-producing spleen or lymph node cells and myeloma cells usually comprise mixing somatic cells with myeloma cells in a 2:1 proportion (though the proportion may vary from about 20:1 to about 1:1), respectively, in the presence of an agent or agents that promote the fusion of cell membranes. It is preferred that the same species of animal serve as the source of the somatic and myeloma cells used in the fusion procedure. Fusion methods have been described by Kohler and Milstein [Nature 256: 495–497 (1975) and Eur. J. Immunol. 6: 511–519 (1976)], and by Gefter et al. [Somatic Cell Genet. 3: 231–236 (1977)]. The fusion-promoting agent used by those investigators were Sendai virus and polyethylene glycol (PEG), respectively. The fusion procedure of the example of the present invention is a modification of the method of Gefter et al. [supra]; PEG is added to the mixture of mouse spleen and myeloma cells to promote the formation of fused cell hybrids. Dimethyl sulfoxide (DMSO), another agent affecting cell membranes, may also be included, in addition to PEG, in the fusion mixture.

4.5. ISOLATION OF CLONES AND ANTIBODY DETECTION

Fusion procedures usually produce viable hybrids at very low frequency. The frequency of heterokaryon formation using state-of-the art techniques with PEG as fusing agent is generally $1\times 10^{-2}$. Ensuing nuclear fusion and formation of synkaryons has a frequency of $1\times 10^{-3}$. Thus only one in $10^5$ fused cells under optimal conditions will yield a vaible hybrid cell line. This frequency, when multiplied by the average frequency of the specific plaque-forming cells in spleen ($1\times 10^{-3}$) yields an overall "success" expectation of about $1\times 10^{-8}$. Therefore, one immune mouse spleen, containing $1-2\times 10^8$ cells, should yield at least one specific hybridoma clone [G. J. Hammerling et al., supra].

Because of the low frequency of obtaining viable hybrids, it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybridomas but prevent the growth of the myeloma cells which normally would go on dividing indefinitely. (The somatic cells used in the fusion do not maintain viability in in vitro culture and hence do not pose a problem.) In the example of the present invention, myeloma cells lacking hypoxanthine phosphoribosyl transferase (HPRT−) are used. These cells are selected against in hypoxanthine/aminopterin/-thymidine (HAT) medium, a medium in which the fused cell hybrids survive due to the HPRT-positive genotype of the spleen cells. The use of myeloma cells with different genetic deficiencies (e.g., other enzyme deficiencies, drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody so that they may be subsequently cloned and propagated. Generally, around 3% of the hybrids obtained produce the desired antibody, although a range of from 1 to 30% is not uncommon. The detection of antibody-producing hybrids can be achieved by any one of several standard assay methods, including enzyme-linked immunoassay and radioimmunoassay techniques which have been described in the literature [R. Kennet, T. McKearn and K. Bechtol (editors), Monoclonal antibodies, hybridomas: a new dimension in biological analyses, pp. 376–384, Plenum Press, New York (1980)]. The detection method used in the example of the present invention was an enzyme-linked immunoassay employing an alkaline phosphatase-conjugated anti-mouse immunoglobin.

4.6. CELL PROPAGATION AND ANTIBODY PRODUCTION

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels; the culture medium, also containing high concentrations of a single specific monoclonal antibody, can be harvested by decantation, filtration or centrifugation.

4.7. IN VITRO DIAGNOSTIC USES FOR MONOCLONAL ANTIBODIES TO CONNECTIVE TISSUE PROTEINS

In Section 2.3., supra, pathological conditions involving connective tissue proteins were enumerated and the changes in collagen profiles of affected tissues and body fluids that occur as the diseases progress were discussed. To illustrate how monoclonal antibodies against specific collagens can be used to diagnose pathological conditions in humans, the following three examples involving (1) non-invasive serological diagnosis of disease, (2) histological diagnosis of disease and (3) cancer detection are offered.

Rheumatoid arthritis and osteoarthrosis produce similar symptoms of pain, stiffness and decreased mobility of the affected joint, e.g., the knee, and hence it is often difficult to evaluate the alteration of joint tissues in the two diseases without further measures. Synovial fluid may be withdrawn from the knee which can be subjected to radioimmunoassays (and immunofluorescent assays for any cell which may be present in the fluid) in which monoclonal antibodies against the various types of collagen are used. If Type II collagen, for instance, is detected in the synovial fluid, this may indicate the destruction of articular cartilage which is characteristic of osterarthrosis, but which also occurs in other erosive joint disorders. On the other hand, if Types I and III collagens are detected, this may be more indicative of the inflammatory-proliferative phase of rheumatoid arthritis. The ability to diagnose early lesions of articular cartilage can effect the choice of the appropriate therapy with which to treat the patient.

The application of monoclonal antibodies conjugated to fluorophores that fluoresce at variable wavelengths to various tissue sections represents a sensitive means of detecting changes in the collagen distribution within biopsied tissue samples. for instance, if liver cirrhosis is suspected, part of the affected tissue can be immunohistologically stained with monoclonal antibodies against Types I, III and IV collagens. Normally, liver contains very little collagen; thus a lack of significant fluorescent staining would indicate a healthy liver. On the other hand, if Type IV collagen was detected in the sample, this would suggest the early stages of cirrhosis. Similarly, if the monoclonal antibodies against Types III and I collagens detected the deposition of such collagens, this would suggest the more advanced stages of the fibrotic disease. [It should be noted that fibrotic diseases affecting the liver and the connective tissue of the organs such as skin and bone can also be detected by serological (i.e., non-biopsy) means utilizing monoclonal antibodies on serum samples.]

One of the most important applications of monoclonal antibodies against connective tissue proteins is for the purpose of early and accurate cancer diagnosis. For example, malignant epithelial cells of breast carcinomas actively produce basement membrane (Type IV) collagen. The production of this collagen continues as the cell metastasizes to other locations, such as the lymph nodes surrounding the breast area. With monoclonal antibodies against Type IV collagen, the presence of a single metastasized cell can be detected immunohistologically in a lymph node biopsy. An early diagnosis of infiltrating cells and lymph node metastasis as judged on the basis of as little as one basement membrane collagen-synthesizing tumor cell is of significant prognostic importance.

Other types of malignancies may also be diagnosed by detecting the neosynthesis of collagens. For instance, monoclonal antibodies against collagens may also prove useful for locating malignant cells in cytological samples such as in Pap smears taken to diagnose cervical and/or uterine cancers. Monoclonal antibodies may also be used in immunohistological differential diagnoses to distinguish, for example, malignant melanomas from benign naevi.

4.8. THERAPY MONITORING USING MONOCLONAL ANTIBODIES AGAINST CONNECTIVE TISSUE PROTEINS

Monoclonal antibodies against connective tissue proteins may be used to monitor the effectiveness of antifibrotic drug therapies. They provide the immunoserological, immunohistological and immunocytological means to detect an inhibition or suppression of collagenous connective tissue neosynthesis, the resulting diminution in the accumulation of the collagenous matrix, and hence, the antifibrotic effect of the drug.

Similarly, monoclonal antibodies may be used to monitor the effectiveness of certain chemotherapies aimed at eradicating malignant tumor cells. For example, tumor cells present in bone marrow malignancies produce the enzyme elastase which selectively cleaves one fourth of the Type III collagen molecule to yield a peptide fragment. If such cells are successfully destroyed by chemotherapeutic means, both elastase and The Type III peptide fragment are released and enter the serum. Detection of this enzyme and peptide in serological samples using monoclonal antibodies provides a sensitive and non-invasive means for monitoring the efficacy of anti-tumor drug therapies.

4.9. ANALYTICAL METHODS

4.9.1. RADIOIMMUNOASSAY

A radioactively labeled connective tissue protein is mixed with monoclonal antibodies specific for that particular protein as antigen and with a serological sample containing an unknown amount of unlabeled connective tissue protein. The labeled and unlabeled antigen compete for binding with the monoclonal antibody. The more unlabeled connective tissue protein there is in the serological sample, the less labeled antigen binds with antibody to form an insoluble complex. By measuring the amount of radioactivity associated with either the insoluble or soluble fractions of the reaction mixture and comparing the values obtained with an appropriately constructed calibration curve (wherein in known amounts of unlabeled and labeled antigen were reacted with antibody), the amount of connective tissue protein in the sample can be accurately quantitated. To facilitate the formation of the insoluble antigen-antibody complex a second antibody directed toward the monoclonal antibody (e.g., goat antimouse immunoglobin G) may have to be added. The addition of the second antibody insures the precipitation of the complex. The insoluble complex may then be separated from the rest of the reaction mixture by centrifugation or filtration.

4.9.2. ENZYME-LINKED IMMUNOSORBENT ASSAY

Connective tissue proteins in serological samples can be measured by a variation of the enzyme-linked immunosorbent assay (ELISA) used to screen hybrids for antibody production (see Section 4.5). Antibodies against connective tissue proteins are first conjugated to an appropriate enzyme, e.g., horseradish peroxidase, alkaline phosphatase or $\beta$-D-galactosidase, generally chosen for the ease with which the enzymatic reaction can be measured. Enzyme-linked antibody preparations of known titer are mixed with serological samples containing unknown amounts of the specific collagen or other connective tissue protein against which the antibody is directed. After an incubation period sufficient to allow for antigen-antibody binding, the mixture is transferred to a microtiter plate, the wells of which have been precoated with connective tissue protein preparations of the same type as that being assayed. Any antibodies remaining unbound after incubation with the test sample bind to the antigen adsorbed to the walls of the microtiter wells. The antigen-antibody complexes that form during the initial incubation can be washed out of the wells of the microtiter plate while the rest of the enzyme-linked antibodies remain complexed to the antigen coating the walls. The next step of the assay is the addition of substrate and measurement of the enzymatic assay. For example, if alkaline phosphatase was conjugated to the antibody preparation, p-nitrophenylphosphate is added to the microtiter wells and the enzymatic reaction is measured spectrophotometrically. With the appropriate controls and standards, the concentration of antigen (connective tissue protein) in the original sample can be quantitated. As the amount of antigen in samples increases, there is less enzyme-linked antibody remaining unbound after incubation with the sample to bind to the antigen coating the microtiter wells and hence the enzymatic reaction will be measurably less.

4.9.3. IMMUNOHISTOLOGICAL AND IMMUNOCYTOLOGICAL STAINING

Slides containing cryostat sections of frozen, unfixed tissue biopsy samples or cytological smears are air dried and incubated with a single monoclonal antibody preparation in a humidified chamber at room temperature. The slides are then layered with a preparation of antibody directed against the monoclonal antibody, usually some type of antimouse immunoglobulin if the monoclonal antibodies used are derived from the fusion of a mouse spleen lymphocyte and a mouse myeloma cell line. This antimouse immunoglobulin is tagged with a compound that fluoresces at a particular wavelength for instance rhodamine. If it is desirable to immunohistologically (or immunocytologically) stain for more than one type of connective tissue protein in a given sample, the slide is then layered with another coating of a second type of monoclonal antibody. This is followed by the application of a second antimouse immunoglobulin tagged with a compound that fluoresces at a different wavelength than the first fluorophore, such as isothiocyanate, and so on until all the connective tissue proteins have been stained. The localization of the connective tissue proteins within the sample is then determined by fluorescent light microscopy and optionally photographically recorded.

4.9.4. IMMUNOELECTRONMICROSCOPY

Under some circumstances it may be necessary to use immunoelectronmicroscopy to detect the presence of collagen and other connective tissue proteins in histological samples. Cryostat sections of tissues, such as skin, are fixed in glutaraldehyde and incubated with the appropriate monoclonal antibody and, subsequently, with antimouse immunoglobulin conjugated with ferritin. The specimens are postfixed in osmium tetroxide, passed through graded alcohols and embedded in Araldite. The blocks are sectioned in a microtome and may be stained with uranyl acetate before electron microscopic examination.

5. EXAMPLES

5.1. CONSTRUCTION OF HYBRIDOMAS SECRETING MONOCLONAL ANTIBODIES TO CONNECTIVE TISSUE PROTEINS

The cell hybridization techniques of this invention are adopted from the protocol of Drs. J. Kearney, A. Anderson and P. Burrows, of the Cellular Immunobiology Unit, 224 Tumor Institute, University of Alabama in Birmingham. [G. J. Hammerling, U. Hammerling and J. F. Kearney (editors), Monoclonal antibodies and T-cell hybridomas in: J. L. Turk (editor), Research Monographs in Immunology, Vol. 3, Elsevier/North Holland Biomedical Press, New York (1981)].

5.1.1. PURIFICATION OF CONNECTIVE TISSUE PROTEINS

Methods for the preparation of the individual types of collagens have been described extensively by Miller and Rhodes [Structural and contractile proteins, in: L. Cunningham and D. Frederiksen (editors), Methods in Enzymology, Academic Press, New York (1981)].

The method used to isolate and purify the collagen-degrading enzyme, elastase, is a modification of the procedure of Mainardi et al. [J. Biol. Chem. 255(24): 12006–12010 (1980)]. A human leukocyte fraction is homogenized, extracted with a neutral buffer, and purified using affinity chromatography on 4-phenylbutylamine Affigel, ion-exchange chromotography on CM-cellulose and gel filtration. Purity and specificity are evaluated by $NaDodSO_4$ electrophoresis and determination of specific activity.

5.1.2. IMMUNIZATION SCHEDULES

At 5 to 6 weeks of age, BALB/c female mice (Jackson Laboratories) are immunized with 200 ug of a purified connective tissue protein as antigen. The antigen is delivered in 0.5 ml of complete Freund's adjuvant by subcutaneous inoculation. An immunization schedule is followed wherein the mice are boosted intraperitoneally with a similar amount of antigen 21 days after the initial priming. Only a single boost is administered, though other immunization schedules with multiple boosts may be used with similar success. The spleens and lymph nodes are removed 4 days after the booster inoculation following standard techniques [Linsenmayer, T. F., Hendrix, M. J. C. and Little, C. D., Proc. Natl. Acad. Sci. U.S.A. 76: 3703–3707 (1979)].

5.1.3. SPLEEN CELL PREPARATION

Spleens of immunized BALB/c mice are removed under sterile conditions and washed in serum-free RPMI 1640 medium (Seromed, Munchen, F.R.G.). The spleens are macerated through cheesecloth and are then resuspended in serum-free RPMI 1640 medium and centrifuged; this washing procedure is performed three times at 4° C. After the final washing, the cells are resuspended in the same medium in a 50 ml sterile tube. The number of cells in the preparation is determined microscopically before mixing with myeloma cells for fusion (see Section 5.4).

5.1.4. MYELOMA CELL PREPARATION

A variant subclone of the mouse myeloma cell line P3-X63-Ag8, isolated by Kearney, et al. [J. Immunol. 123(4): 1548–1550 (1979)] and designated X63-Ag8.653, is maintained in Dulbecco's MEM or RPMI 1640 medium (Seromed, Munchen, F.R.G.) supplemented with 15% fetal calf serum, 2 mM glutamine, 50 uM 2-mercaptoethanol (Merck, Darmstadt, F.R.G.), 100 units/ml penicillin, 100 ug/ml streptomycin, and 0.25 ug/ml Fungizone (Flow Laboratories, Bonn, F.R.G.) (hereinafter called "complete medium"). Like its parent, X630-Ag8.653 is a hypoxanthine/aminopterin/thymidine-(HAT)-sensitive cell line. However, unlike its parent, X-63-Ag8.653 has lost immunoglobulin expression entirely and does not synthesize 1 or K chains of X63 origin upon fusion with antibody-forming cells. The myeloma cells are cultured in complete medium and harvested during the exponential phase of growth. Harvested cells are transferred to 50 ml sterile tubes and are washed three times in serum-free RPMI 1640 medium at 4° C. The cells are counted microscopically prior to fusion with spleen cells.

5.1.5. FUSION PROCEDURE

Spleen cells and X63-Ag8.653 myeloma cells are combined in a ratio of 2:1 or 1:1 (spleen cells:myeloma cells) and washed once in serum-free RPMI 1640 medium at 37° C. The cell mixture is centrifuged at room temperature at 1,000 rpm for 7 minutes. The pellet fraction is carefully aspirated to leave it as dry as possible. Next, the pellet is loosened by gentle tapping and is resuspended with gentle agitation in 1.0 to 1.5 ml of PEG-4000 (polyethylene glycol) solution at 37° C. The PEG-400 solution is prepared by autoclaving 20 gm PEG 4000 in a 100 ml bottle, cooling and adding 28 ml of sterile phosphate buffered saline. After approximately 30 seconds, the cell mixture is slowly diluted dropwise to a volume of roughly 20 ml with serum-free RPMI 1640 medium at 37° C.; the tube is then filled to 50 ml with the same medium. The cells are centrifuged at room temperature and resuspended at 37° C. in HAT medium, which is selective for fused cells. HAT medium is prepared by adding 1 ml of a stock solution (100×) of hypoxanthine (H) and thymidine (t) and 1 ml of a stock solution (100×) of aminopterin (A) to 100 ml of complete medium. The HT stock contains 272.2 mg hypoxanthine and 7.75 mg thymidine in 200 ml distilled water. Because the hypoxanthine does not dissolve well, the pH of the solution is adjusted to pH 8.1–8.5 with 1–2 drops of 1N NaOH. The solution is sterilized through a 0.45 u Millipore filter and stored at 4° C. The A stock contains 3.52 mg aminopterin in 200 ml distilled water. It is also sterilized by Millipore filtration and stored at 4° C.

The cell mixture is resuspended in HAT medium at a concentration of about 2 to $5 \times 10^5$ spleen cells/ml. Care is taken not to break up cell clumps. Peritoneal exudate feeder cells are then added (roughly, the peritoneal washout of one normal, non-immunized mouse per 100 ml of HAT/fused-cell suspension) and 1 ml of the cell suspension is added per well of a 24 well macrotiter plate (Costar, Cambridge, Mass.).

5.1.6. OUTGROWTH AND SELECTION

After 4 or 5 days in the selective HAT medium, the cells are observed with an inverted microscope to check for myeloma cell death. (The X63-Ag8.653 cell line is HAT-sensitive and thus, unfused myeloma cells cannot survive in this medium; unfused spleen cells naturally die out of the culture.) Contamination of the wells is also checked for and any contaminated wells are killed with a copper sulfate solution.

The fused cells are allowed to incubate in HAT medium for two weeks at which time 0.5 ml of the supernatant of each well is discarded and replaced with 0.5 ml of complete (non-HAT) medium. This medium replenishment is repeated daily for another week. Two to three days after the last medium replenishment, which is enough time to allow for sufficient production of antibodies for testing, the macrotiter plates are scored for hybrid growth and assayed for antibody activity by the ELISA method described in Section 5.1.7.

5.1.7. IMMUNOLOGICAL CHARACTERIZATION OF HYBRID-PRODUCED MONOCLONAL ANTIBODIES

The identification of those hybrids synthesizing antibodies which recognize the connective tissue protein used as antigen is accomplished using a modification of the enzyme-linked immunosorbent assay (ELISA) [Engvall, E. and Perlman, P., Immunochem. 8: 871–876 (1971)] as detailed by Kearney et al. [J. Immunol. 123: 1548–1550 (1979)].

The wells of a 96-well polyvinyl microtiter plate are coated with 100 ul/well of 1 mg/ml solution of collagen antigen in borate saline. The plate is incubated for four hours at 25° C. or overnight and 4° C. The plates are then blocked with 1% bovine serum albumin (BSA) in borate buffered saline (BS-BSA) and incubated for one hour at 25° C. The wells of the microtiter plate are washed twice with saline, after which the supernatants (containing monoclonal antibodies) from the wells of the macrotiter plates used for outgrowth and selection of fused hybrids are added to the microtiter wells. The plate is incubated for four hours at 25° C. (or overnight at 4° C.) and washed two to three times with saline. To each well, 100 ul of alkaline phosphatase-labeled antibodies (goat antimouse-immunoglobulin) diluted 1:500 in BS-BSA is added. After incubating for four hours at 25° C. or overnight at 4° C., the wells are washed 4–5 times with saline and 200 ul of substrate (p-nitrophenylphosphate) is added per well. The reaction is stopped by the addition of 50 ul 3N NaOH to each well. The absorbance of the fluid in the wells is then determined spectrophotometrically.

In those wells to which monoclonal antibodies from the culture supernatants bind and to which the enzyme-linked goat antimouse-immunoglobulin subsequently bind, the alkaline phosphatase converts colorless p-nitrophenylphosphate into yellow p-nitrophenol. The colorometric reaction permitts the easy identification of those culture supernatants containing collagen-specific antibodies and hence the identification of the desired fused hybrids. This step is performed to exclude from further analysis those hybrids that do not produce immunoglobulin and those that synthesize antibodies not specific for the collagen protein antigen.

5.1.8. CLONING OF HYBRIDS

The extent of hybrid cell growth in the wells of the macrotiter plates (see Section 5.1.6.) is determined 3–4 weeks after the initial plating in HAT medium. The cell suspensions were agitated gently and 2–5 ul are diluted from each well into 30 ml of complete medium containing peritoneal exudate feeder cells. Into each well of a 96-well costar microtiter plate, 200 ul of the diluted cell suspension are distributed. This suspension is diluted further by delivering 10 ml in 20 or 30 ml of medium containing feeder cells and 200 ul aliquots are added to each well of another microtiter plate. Further dilutions of the cell suspension can be performed if necessary. This method is used to insure that the wells of at least one plate contain clones derived from a single cell. Samples of cells from the original hybridoma-containing macrotiter wells are frozen for safekeeping.

After a sufficient time for growth of the hybridoma cells (clones), the supernatants of the microtiter wells are rescreened for monoclonal antibody production using the ELISA assay described in Section 5.1.7.

5.1.9. STABILITY OF PHENOTYPE DETERMINATION

Those hybrids identified to be specific antibody producers are transferred to new Costar plates at low cell density (approximately 5 cells/well) containing fetal calf serum and feeder cells. Approximately two weeks after this seeding, the culture supernatants from wells containing viable hybrids are assayed using the ELISA method of Section 5.1.7. to determine which hybrids have maintained a stable phenotype. Hybrids that continued to synthesize specific antibodies are then cloned by transferring diluted cell suspensions to new Costar plates at a concentration of one hybrid cell per three to five wells. Surviving hybrids are screened and those continuing to demonstrate antibody production are recloned to insure that the antibodies produced arise from a single fused hybrid and hence are monospecific.

5.1.10. DETERMINATION OF MONOCLONAL ANTIBODY SPECIFICITY

The culture media from hybrids that survived two successive clonings and that continued to exhibit a stable phenotype are screened for cross-reactivity against the other types and individual molecular forms of collagen as well as other connective tissue proteins using the ELISA assay of Section 5.1.7. Instead of using the antigen against which the monoclonal antibody was raised to coat the wells of the Costar plates, the other individual collagens and connective tissue proteins are used in the ELISA assay. Only those monoclonal antibodies exhibiting no cross-reactivity are used in the procedures for detecting connective tissue proteins in body fluids and tissue samples described in Sections 5.2, 5.3, and 5.4 below.

5.1.11. PROPAGATION OF HYBRID CELLS AND ANTIBODY PRODUCTION

Hybrids which synthesized antibodies of the desired specificity are amplified in cell culture and stored in liquid nitrogen so that an adequate supply of cells producing identically monospecific antibodies are available. To propagate the hybrids, samples of the fused cells are injected intraperitoneally into BALB/c mice ($10^6$ cells/mouse) resulting in the subsequent induction of palpable tumors within a few weeks. The tumors generally produce ascites fluid (approximately 2 ml per mouse) containing antibody amounts significantly greater (as high as 60 mg per mouse) than those obtained by in vitro cell culture techniques. Sera samples from the inoculated mice contain antibody titers comparable so that of ascites fluid. The mouse hybridoma-produced monoclonal antibodies are purified by subjecting samples of ascites fluid, sera, or media to immunoadsorption chromatography.

5.2. DETECTION AND MEASUREMENT OF CONNECTIVE TISSUE PROTEINS IN BIOLOGICAL FLUIDS WITH MONOCLONAL ANTIBODIES

5.2.1. RADIOIMMUNOASSAY

Iodinated connective tissue protein antigens are prepared as described by Rohde et al. and are used in a modification of the radioimmunoassay described by the same authors [J. Immunol. Meth. 11: 135–145 (1976)]. Antibody titrations are carried out by diluting the monoclonal antibody preparation with PBS. Duplicate tubes containing 0.1 ml monoclonal antibody preparation (ascites fluid or tissue culture fluid), 0.1 ml labeled antigen, and 0.2 ml 1% BSA dissolved in PBS are incubated for 24 hours at 4° C. After mixing with 0.5 ml antiserum to mouse Ig, the incubation is continued for an additional 24 hours at 4° C. Insoluble material is collected by centrifugation and the precipitate is washed three times with cold PBS/BSA prior to counting. Non-specific precipitation of labeled antigen is determined by replacing the monoclonal antibody preparation by non-immune Ig. Antigen binding capacity of the monoclonal antibody preparation is calculated according to Minden and Farr [D. M. Weir, (editor) Handbook of Experimental Immunology, Blackwell, Oxford, England, p. 151].

In the competition assay, sufficient monoclonal antibody is used to bind 80% of the labeled antigen. However, the monoclonal antibody preparation is first incubated with a sample containing unlabeled connective tissue protein at 4° C. for 24 hours and then the labeled antigen is added to the reaction, followed by incubation and finally addition of and incubation with anti-mouse Ig as above. Precipitable counts are measured, also as above in a Beckman Gamma 300 counter.

5.2.2. ENZYME-LINKED IMMUNOSORBENT ASSAY

Monoclonal antibodies directed against connective tissue proteins are conjugated to alkaline phosphatase by the method of Hammerling et al. [Monoclonal antibodies and T-cell hybridomas in: J. L. Turk (editor) Research Monographs in Immunology, Vol. 3, Elsevier/North Holland Biomedical Press, New York (1981)]. Dialysis tubing is boiled for 20 minutes in deionized water. Alkaline phosphatase (1.5 mg as an ammonium sulfate-precipitated slurry) is centrifuged at 4° C. for 2–3 minutes at 12,000 xg and the supernatant is discarded. The pelleted enzyme is dissolved in buffer (Dulbecco's PBS with magnesium and calcium cations, DPBS) containing an appropriate amount of monoclonal antibody, in a volume of approximately 0.2 ml. The antibody-enzyme mixture is dialyzed against 100 ml of DPBS overnight at 4° C. The contents of the dialysis tubing are washed out into a graduated glass tube and the volume is adjusted to 0.5 ml with DPBS. Next, 25% glutaraldehyde is added to a final concentration of 0.2% (4 ul for 0.5 ml). The mixture is gently agitated on a Vortex mixer and is incubated for 2 hours at room temperature. After dialyzing overnight against DPBS at 4° C., the enzyme-coupled antibody is diluted to 10 ml with 5% BSA-0.05M Tris buffer, which serves as a stock solution.

Enzyme-linked monoclonal antibodies thus prepared are mixed with serological samples containing unknown amounts of the specific connective tissue protein being assayed. The mixtures are transferred to the wells of microtiter plates pre-coated with the appropriate antigen and the enzyme activity of the conjugated alkaline phosphase is measured as described in Section 5.1.7.

5.3. IMMUNIHISTOLOGICAL APPLICATION OF MONOCLONAL ANTIBODIES AGAINST CONNECTIVE TISSUE PROTEINS

5.3.1 IMMUNOFLUORESCENT STAINING OF BIOPSIED TISSUE SECTIONS

Sections of tissues 4–6 um thick are prepared from frozen, unfixed biopsy samples by cryostat sectioning. The air-dried sections are incubated with a particular monoclonal antibody. For controls, sections are incubated with immunoglobulin (Ig) from pre-immune serum. After 30 minutes of incubation in a humidified chamber at room temperature, the sections are rinsed three times with phosphate-buffered saline (PBS, pH 7.4) and, in a second step, layered with a 1:30 dilution of fluorescein-isothiocyanate conjugated (FITC) rabbit anti-mouse Ig for 30 minutes. Finally, the slides are washed exhaustively to remove nonspecifically associated reagents and are sealed with a solution of 90% glycerol/10% PBS under a coverslip. The localization of staining is observed and photographed using a Leitz-fluorescence microscope equipped with a K2 filter system for FITC.

5.3.2. IMMUNOELECTRONMICROSCOPY

When immunoelectronmicroscopy is performed on skin biopsies, the skin specimens are cut into slices 0.2 to 0.5 mm thick with 2 razor blades or with a cryostat. They are fixed in 1% glutaraldehyde in 0.16M cacodylate buffer, pH 7.4, at 4° C. for 20 minutes [R. Fleischmajer et al., J. Invest. Dermat. 75:189–191 (1980)], washed several times with 0.15M Tris-HCl buffer, pH 7.5 to remove the excess glutaraldehyde and stored in that buffer at 4° C. Incubations with monoclonal antibodies are carried out for 24 hr at 4° C. with rabbit anti-mouse Ig antibodies tagged with ferritin, diluted 1:5 in PBS, pH 7.2. The specimens are rinsed with 0.1M Tris-HCl buffer, pH 7.5 for 24 hr at 4° C., washed 3 times with 0.16M cacodylate buffer, pH 7.5, and fixed in 3% glutaraldehyde in 0.16M cacodylate buffer, pH 7.4, for 2 hr. Control specimens are treated only with rabbit anti-mouse Ig ferritin-tagged antibodies. The specimens are postfixed in osmium tetroxide, passed through graded alcohols and embedded in Araldite. The blocks are sectioned in a LKB ultratome-4 microtome and the specimens, about 500–600 A thick, are either left unstained or are stained with a saturated solution of uranyl acetate. The grids are examined with a Hitachi HU-12A or with a Phillips 300 electron microscope.

Other tissues, for instance kidney, are fixed in phosphate buffered 4% paraformaldehyde at 4° C. for 2 hours with one change [Gay et al., Collagen Rel. Res. 1:370–377 (1981)]. Tissues are then washed for 36 hours in PBS with 4% sucrose at 4° C. with multiple changes.

The last wash is performed in PBS with 4% sucrose and 5% glycerol for 1 hour. Tissues are then placed in OCT freezing medium with a cork or plastic backing to hold them and quickly frozen by immersing them in a jar of methylbutane (isopentane) placed in a small chamber of liquid nitrogen. The frozen tissues are then wrapped in aluminum foil and stored in a closed container at −20° C. Frozen sections 8 um thick are cut and placed in albumin coated slides and air-dried for at least 5 minutes. Slides are then placed in a solution of ice-cold $NaBH_4$ (10 mg/100 ml) in PBS for 1 hour with one change. Following this procedure, the slides are washed at 4° C. in PBS, 3 changes for 30 minutes each.

Tissue sections are reacted with the appropriate monoclonal antibody in a moist chamber overnight at 4° C. or at room temperature for 2 hours. Slides are washed thoroughly with PBS and then incubated an additional 2 hours with secondary antibody (goat or rabbit anti-mouse Ig). This is followed by washing with cold PBS and a third antibody treatment with Fab-peroxidase-anti-peroxidase (Fab-PAP) for 3 hours. The Fab-PAP solution is removed by washing with PBS and the tissue sections are incubated in 150 ml of 0.1M Tris, pH 7.6, containing 40 mg of 3,3-diaminobenzidine tetrahydrochloride and 15 ul of 5% $H_2O_2$ for 15–18 minutes. Slides are then washed with cold PBS and stained with 1% osmium tetroxide for 1 hour at room temperature. The stained slides are again rinsed with cold PBS, dehydrated in acetone, embedded in Maraglas ® (70%) and ultra-thin sections are made for examination using a Zeiss EM 10 electron microscope.

5.4. IMMUNOCYTOLOGICAL APPLICATION OF MONOCLONAL ANTIBODIES AGAINST CONNECTIVE TISSUE PROTEINS

To determine the production of collagens and the type of collagen synthesized by cells such as skin fibroblasts which can be cultivated in vitro by standard cell culture techniques, the following procedure is used. Anchorage-dependent cells which have grown to confluent monolayers on solid supports are detached by exposure to trypsin and are replated in the Dulbecco-Vogt modification of Eagle's medium containing 10% fetal calf serum in 35×10 mm Falcon plastic tissue culture dishes. The dishes are incubated at 37° C. under a 5% $CO_2$/95% air atmosphere. About 6 hours later, the medium in each dish is replaced with fresh media which in some cases contained 50 ug/ml of newly dissolved ascorbic acid. These media are replaced every day. At various times after plating the cells, dishes are taken for analysis, the media are removed, and the dishes are rinsed at least four times with 0.15M NaCl, 0.05M Tris-HCl pH 7.4.

The air-dried culture dishes are rinsed with acetone and allowed to dry. Purified monoclonal antibodies dissolved in 0.15M NaCl, 0.02M sodium phosphate, pH 7.4, are added to the dishes and allowed to react for 2 hours at 20° C. Controls are run to assess the nonspecific associations of reagents with the cells. Such control experiments indicated that the nonspecific association of label is negligible. Subsequently, the dishes are rinsed three times with 0.15M NaCl, 0.02M sodium phosphate, pH 7.4, and are layered with 1 ml of a 1:32 dilution of fluorescein-isothiocyanate-conjugated rabbit antimouse Ig. When cell samples are simultaneously stained for two antigens, the dishes are first exposed to one type of monoclonal antibody against a connective tissue protein and then to the fluorescein-isothiocyanate-conjugated rabbit antimouse Ig. Subsequently, the dishes are exposed to monoclonal antibodies against a different type of connective tissue protein, washed, and then reacted with rhodamine-conjugated rabbit antimouse Ig. Finally, all dishes are washed extensively to remove adventitiously associated reagents and sealed from the air with a solution of 90% glycerol/10% saline under a cover slip. The localization of fluorescent stains on the dishes is observed in a Zeiss Universal fluorescence microscope and recorded photographically.

I claim:

1. A method for immunochemically monitoring the effectiveness of cancer therapy in a human cancer patient, comprising:
    (a) reacting a first serum sample taken from said patient prior to initiation of therapy with a known titer of a soluble monoclonal antibody specific for a connective tissue protein which is released by tumor cells of said cancer and is present in an unknown amount in said serum sample;
    (b) allowing said antibodies and connective tissue protein to interact to form antigen-antibody complexes in the reaction mixture;
    (c) measuring the amount of antigen-antibody complexes formed to determine the amount of said connective tissue protein present in said reaction mixture;
    (d) repeating each of said steps on a second serum sample taken from said patient subsequent to the initiation of therapy; and
    (e) comparing the amount of said connective tissue protein in said first and second serum samples to determine whether said connective tissue protein has decreased in the interval between the taking of the first and second serum samples, where a decrease reflects successful therapy, thereby monitoring the effectiveness of such therapy in said patient.

2. The method for immunochemically monitoring the effectiveness of cancer therapy in accordance with claim 1 in which said monoclonal antibody is enzyme-labelled and the amount of antigen-antibody complexes formed in each of the first and second sample reaction mixtures is measured by enzyme-linked immunosorbent assay.

3. The method for immunochemically monitoring the effectiveness of cancer therapy in accordance with claim 2 in which said monoclonal antibody is enzyme-labelled and the amount of antigen-antibody complexes formed in each of the first and second sample reaction mixtures is measured by
    (a) removing uncomplexed enzyme-labelled antibodies from each of said reaction mixtures by contacting said reaction mixtures with a surface to which said connective tissue protein is bound and allowing uncomplexed enzyme-labelled antibody-antigen complexes to form on said surface;
    (b) removing the enzyme-labelled antibody-antigen complexes formed in step (b) of claim 87 from said surface; and
    (c) contacting the enzyme-labelled monoclonal antibodies complexed to the surface-bound connective tissue protein with a substrate of the enzyme, measuring enzyme activity and quantitatively determining the amount of said connective tissue protein in the first and second samples with a standard curve constructed with known amounts of connective tissue protein of the same type as that released by said tumor cells.

4. The method for immunochemically monitoring the effectiveness of cancer therapy in accordance with claim 1 in which a known amount of such connective tissue protein bearing a radioactive label is added to the first and second serum samples and the amount of antigen-antibody complexes formed in each of the first and second sample reaction mixtures is measured by radioimmunoassay.

5. The method for immunochemically monitoring the effectiveness of cancer therapy in accordance with claim 4 in which a known amount of said connective tissue protein bearing a radioactive label is added after the monoclonal antibody specific for said connective tissue protein has been added to the first and second serum samples and the amount of antigen-antibody complexes formed in each of the first and second sample reaction mixtures is measured by
(a) adding a preparation of anti-immunoglobulin to each of said reaction mixtures to form immune complexes with the antigen-antibody complexes; and
(b) separating the immune complexes so formed from supernatant fractions of the reaction mixtures, measuring the radioactivity of the immune complexes or the supernatant fractions and quantitatively determining the amount of said connective tissue protein in the samples with a standard curve constructed with known amounts of radioactively-labelled connective tissue protein of the same type as that released by said tumor cells.

6. The method for immunochemically monitoring the effectiveness of cancer therapy in accordance with any one of claims 1-5 in which the tumor cells are osteosarcoma cells and the connective tissue protein released by the cells is Type I collagen.

7. The method for immunochemically monitoring the effectiveness of cancer therapy in accordance with any one of claims 1-5 in which the tumor cells are chondrosarcoma cells and the connective tissue protein released by the cells is Type II collagen.

8. The method for immunochemically monitoring the effectiveness of cancer therapy in accordance with any one of claims 1-5 in which the tumor cells are breast carcinoma cells and the connective tissue protein released by the cells is Type IV collagen.

9. The method for immunochemically monitoring the effectiveness of cancer therapy in accordance with any one of claims 1-5 in which the tumor cells are bone marrow cells and the connective tissue protein released by the cells is elastase or Type III collagen peptide.

10. The method for immunochemically monitoring the effectiveness of cancer therapy in accordance with claim 2 or 3 in which the enzyme is alkaline phosphatase with p-nitrophenylphosphate as a substrate.

11. A method for immunochemically monitoring the effectiveness of anti-inflammatory and/or antifibrotic therapy in a human patient afflicted with an inflammatory and/or fibrotic disease or suffering from overt trauma, comprising:
(a) reacting a first serum or synovial fluid sample taken from such patient prior to initiation of therapy with a known titer of a soluble monoclonal antibody specific for a connective tissue protein which is released in an organ or tissue affected by said disease or overt trauma and is present in an unknown amount in such serum or synovial fluid sample;
(b) allowing such antibodies and connective tissue protein to interact to form antigen-antibody complexes in the reaction mixture;
(c) detecting said antigen-antibody complexes or measuring the amount of said antigen-antibody complexes formed to determine the amount of said connective tissue protein present in said reaction mixture;
(d) repeating each of said steps on a second serum or synovial fluid sample taken from said patient subsequent to the initiation of therapy; and
(e) comparing the amount of said connective tissue protein in said first and second serum or synovial fluid samples to determine whether said connective tissue protein has decreased in the interval between the taking of the first and second serum samples, where a decrease reflects successful therapy, thereby monitoring the effectiveness of said therapy in said patient.

12. The method of immunochemically monitoring the effectiveness of anti-inflammatory and/or antifibrotic therapy in accordance with claim 11 in which said monoclonal antibody is enzyme-labelled and the amount of antigen-antibody complexes formed in each of the first and second sample reaction mixtures is measured by enzyme-linked immunosorbent assay.

13. The method for immunochemically monitoring the effectiveness of anti-inflammatory and/or antifibrotic therapy in accordance with claim 12 in which said monoclonal antibody is enzyme-labelled and the amount of antigen-antibody complexes formed in each of the first and second sample reaction mixtures is measured by
(a) removing uncomplexed enzyme-labelled antibodies from each of said reaction mixtures by contacting said reaction mixtures with a surface to which said connective tissue protein is bound and allowing uncomplexed enzyme-labelled antibody-antigen complexes to form on said surface;
(b) removing the enzyme-labelled antibody-antigen complexes formed in step (b) of claim 11 from said surface; and
(c) contacting the enzyme-labelled monoclonal antibodies complexed to the surface-bound connective tissue protein with a substrate of the enzyme, measuring enzyme activity and quantitatively determining the amount of said connective tissue protein in the first and second samples with a standard curve constructed with known amounts of connective tissue protein of the same type as that released in the organ or tissue affected by such disease or overt trauma.

14. The method for immunochemically monitoring the effectiveness of anti-inflammatory and/or antifibrotic therapy in accordance with claim 11 in which a known amount of said connective tissue protein bearing a radioactive label is added to the first and second serum or synovial fluid samples and the amount of antigen-antibody complexes formed in each of the first and second sample reaction mixtures is measured by radioimmunoassay.

15. The method for immunochemically monitoring the effectiveness of anti-inflammatory and/or antifibrotic therapy in accordance with claim 14 in which a known amount of said connective tissue protein bearing a radioactive label is added after the monoclonal antibody specific for such connective tissue protein has been added to the first and second serum or synovial fluid samples and the amount of antigen-antibody complexes formed in each of the first and second sample reaction mixtures is measured by (a) adding a preparation of anti-immunoglobulin to each of said reaction mixtures to form immune complexes with the antigen-antibody complexes; and (b) separating the immune complexes so formed from supernatant fractions of the reaction mixtures, measuring the radioactivity of the immune complexes or the supernatant fractions, and quantitatively determining the amount of said connective tissue protein in the samples with a standard curve constructed with known amounts of radioactively-labelled connective tissue protein of the same type as that released in the organ or tissue affected by said disease or overt trauma.

16. The method for immunochemically monitoring the effectiveness of anti-inflammatory and/or antifibrotic therapy in accordance with any one of claims 11–15 in which the fibrotic disease is atherosclerosis, the samples are serum samples and the connective tissue protein is Type I, III, IV or V collagen.

17. The method for immunochemically monitoring the effectiveness of anti-inflammatory and/or antifibrotic therapy in accordance with any one of claims 11–15 in which the fibrotic disease is liver fibrosis or cirrhosis, the samples are serum samples and the connective tissue protein is Type I, III or IV collagen.

18. The method for immunochemically monitoring the effectiveness of anti-inflammatory and/or antifibrotic therapy in accordance with any one of claims 11–15 in which the fibrotic disease is scleroderma, the samples are serum samples and the connective tissue protein is Type I, III or IV collagen.

19. The method for immunochemically monitoring the effectiveness of anti-inflammatory and/or antifibrotic therapy in accordance with any one of claims 11-15 in which the fibrotic disease is rheumatoid arthritis in the inflammatory-proliferative phase, the samples are synovial fluid samples and the connective tissue protein is Type I, II, III, IV or V collagen.

20. A method for immunochemically monitoring the effectiveness of cancer therapy in a human cancer patient, comprising:

(a) reacting a first histological or cytological sample taken from said patient prior to initiation of therapy with a soluble monoclonal antibody specific for a connective tissue protein which is released by tumor cells of said cancer and is present in said sample;

(b) allowing said antibodies and connective tissue protein to interact to form antigen-antibody complexes in said histological or cytological sample;

(c) detecting the antigen-antibody complexes formed in said histological or cytological sample;

(d) repeating each of said steps on a second said sample taken from said patient subsequent to the initiation of therapy; and (e) comparing the connective tissue protein detected in said first and second histological or cytological samples to determine whether said connective tissue protein has decreased in the interval between the taking of the first and second samples, where a decrease reflects successful therapy, thereby monitoring the effectiveness of said therapy in such patient.

21. The method for immunochemically monitoring the effectiveness of cancer therapy in accordance with claim 20 in which the antigen-antibody complexes formed in each of the first and second histological or cytological samples are detected by the use of a labelled anti-immunoglobulin.

22. The method for immunochemically monitoring the effectiveness of cancer therapy in accordance with claim 21 in which the antigen-antibody complexes formed in each of the first and second histological or cytological samples are detected by (a) layering onto said samples containing said antigen-antibody complexes a preparation of anti-immunoglobulin labelled by conjugation to a fluorescent compound;

(b) allowing such anti-immunoglobulin to form immune complexes with the antigen-antibody complexes; and (c) detecting the presence of said connective tissue protein by observing the fluorescence of said anti-immunoglobulin-antigen-antibody complexes by fluorescent light microscopy.

23. The method for immunochemically monitoring the effectiveness of cancer therapy in accordance with any one of claims 20–22 in which the histological sample is an osteosarcoma sample and the connective tissue protein released by the cells is Type I collagen.

24. The method for immunochemically monitoring the effectiveness of cancer therapy in accordance with any one of claims 20–22 in which the histological sample is a chondrosarcoma sample and the connective tissue protein released by the cells is Type II collagen.

25. The method for immunochemically monitoring the effectiveness of cancer therapy in accordance with any one of claims 20–22 in which the histological sample is a breast carcinoma sample and the connective tissue protein released by the cells is Type IV collagen.

26. The method for immunochemically monitoring the effectiveness of cancer therapy in accordance with any one of claims 20–22 in which the cytological sample is a Pap smear containing cervical and/or uterine tumor cells and the connective tissue protein released by the cells is Type IV collagen.

27. The method for immunochemically monitoring the effectiveness of anti-inflammatory and/or antifibrotic therapy in accordance with claim 11 in which the antigen-antibody complexes formed in each of said first and second serum or synovial fluid samples are detected by the use of a labelled anti-immunoglobulin.

28. The method for immunochemically monitoring the effectiveness of anti-inflammatory and/or antifibrotic therapy in accordance with claim 27 in which the antigen-antibody complexes formed in each of the first and second serum or synovial fluid samples are detected by (a) layering onto synovial exudate smears taken from each of said synovial fluid samples containing said antigen-antibody complexes a preparation of anti-immunoglobulin labelled by conjugation to a fluorescent compound;

(b) allowing said anti-immunoglobulin to form immune complexes with said antigen-antibody complexes; and (c) detecting said connective tissue protein by observing fluorescence of said anti-immunoglobulin-antigen-antibody complexes by fluorescent light microscopy.

29. The method for immunochemically monitoring the effectiveness of anti-inflammatory and/or antifibrotic therapy in accordance with claim 27 or 28 in which the inflammatory disease is rheumatoid arthritis and the connective tissue protein released is Type I, II, III, IV or V collagen.

30. A method for immunochemically monitoring the effectiveness of anti-inflammatory and/or antifibrotic therapy in a human patient afflicted with an inflammatory and/or fibrotic disease, comprising:
   (a) reacting a first histological sample taken from said patient prior to initiation of therapy with a soluble monoclonal antibody specific for a connective tissue protein which is produced by neosynthesis during the course of said disease and is present in said histological sample;
   (b) allowing said antibodies and connective tissue protein to form antigen-antibody complexes in said histological sample;
   (c) detecting the antigen-antibody complexes formed in said histological sample;
   (d) repeating each of said steps on a second histological sample taken from said patient subsequent to the initiation of therapy; and
   (e) comparing the connective tissue protein detected in said first and second histological samples to determine whether said connective tissue protein has decreased in the interval between the taking of the first and second histological samples, where a decrease reflects successful therapy, thereby monitoring the effectiveness of said therapy in said patient.

31. The method for immunochemically monitoring the effectiveness of anti-inflammatory and/or antifibrotic therapy in accordance with claim 30 in which the antigen-antibody complexes formed in each of said first and second histological samples are detected by the use of a labelled anti-immunoglobulin.

32. The method for immunochemically monitoring the effectiveness of anti-inflammatory and/or antifibrotic therapy in accordance with claim 31 in which the antigen-antibody complexes formed in each of said first and second histological samples are detected by
   (a) layering onto each of said histological samples containing said antigen-antibody complexes a preparation of anti-immunoglobulin labelled by conjugation to a fluorescent compound;
   (b) allowing said anti-immunoglobulin to form immune complexes with said antigen-antibody complexes; and
   (c) detecting such connective tissue protein by observing fluorescence of said anti-immunoglobulin-antigen-antibody complexes by fluorescent light microscopy.

33. The method for immunochemically monitoring the effectiveness of anti-inflammatory and/or antifibrotic therapy in accordance with any one of claims 30-32 in which said fibrotic disease is atherosclerosis, the histological samples are blood vessel tissue samples and the connective tissue protein is Type I, III, IV or V collagen.

34. The method for immunochemically monitoring the effectiveness of anti-inflammatory and/or antifibrotic therapy in accordance with any one of claims 30-32 in which said fibrotic disease is liver fibrosis or cirrhosis, the histological samples are liver tissue samples and the connective tissue protein is Type I, III or IV collagen.

35. The method for immunochemically monitoring the effectiveness of anti-inflammatory and/or antifibrotic therapy in accordance with any one of claims 30-31 in which said fibrotic disease is scleroderma, the histological samples are skin tissue samples and the connective tissue protein is Type I, III or IV collagen.

36. The method for immunochemically monitoring the effectiveness of anti-inflammatory and/or antifibrotic therapy in accordance with any one of claims 30-32 in which such inflammatory disease is rheumatoid arthritis, the histological sample is a synovial tissue or pannus tissue sample and the connective tissue protein is Type I, III, IV or V collagen.

37. A method for immunochemically detecting or following the pathogenesis of a disease in a human patient suspected or known to have such disease, comprising:
   (a) reacting a first serum or synovial fluid sample taken from such patient with a known titer of a soluble monoclonal antibody specific for a connective tissue protein which is released in an organ or tissue affected by such disease and is present in an unknown amount in such sample;
   (b) allowing such antibodies and connective tissue protein to interact to form antigen-antibody complexes in the reaction mixture;
   (c) measuring the amount of antigen-antibody complexes formed to determine the amount of such connective tissue protein present in such reaction mixture;
   (d) repeating each of such steps on a second, control sample which is known to reflect a non-pathological or a particular pathological condition in human beings; and
   (e) comparing the amount of such connective tissue protein in such first and second serum or synovial fluid samples to determine whether the amount of such connective tissue protein in such first sample reflects a presence or progression of such disease, thereby detecting or following the pathogenesis of such disease in such patient.

38. The method for immunochemically detecting or following the pathogenesis of a disease in accordance with claim 37 in which such monoclonal antibody is enzyme-labelled and the amount of antigen-antibody complexes formed in each of the first and second sample reaction mixtures is measured by enzyme-linked immunosorbent assay.

39. The method for immunochemically detecting or following the pathogenesis of a disease in accordance with claim 38 in which such monoclonal antibody is enzyme-labelled and the amount of antigen-antibody complexes formed in each of the first and second sample reaction mixtures is measured by
   (a) removing uncomplexed enzyme-labelled antibodies from each of such reaction mixtures by contacting such reaction mixtures with a surface to which such connective tissue protein is bound and allowing uncomplexed enzyme-labelled antibody-antigen complexes to form on such surface;
   (b) removing the enzyme-labelled antibody-antigen complexes formed in step (b) of claim 37 from such surface; and
   (c) contacting the enzyme-labelled monoclonal antibodies complexed to the surface-bound connective tissue protein with a substrate of the enzyme, measuring enzyme activity and quantitatively determining the amount of such connective tissue protein in the first and second samples with a standard curve constructed with known amounts of connective tissue protein of the same type as that released in the organ or tissue affected by such disease.

40. The method for immunochemically detecting or following the pathogenesis of a disease in accordance with claim 37 in which a known amount of such connective tissue protein bearing a radioactive label is added to the first and second serum or synovial fluid samples and the amount of antigen-antibody complexes formed in each of the first and second sample reaction mixtures is measured by radioimmunoassay.

41. The method for immunochemically detecting or following the pathogenesis of a disease in accordance with claim 40 in which a known amount of such connective tissue protein bearing a radioactive label is added after the monoclonal antibody specific for such connective tissue protein has been added to the first and second serum or synovial fluid samples and the amount of antigen-antibody complexes formed in each of the first and second sample reaction mixtures is measured by
   (a) adding a preparation of anti-immunoglobulin to each of such reaction mixtures to form immune complexes with the antigen-antibody complexes; and
   (b) separating the immune complexes so formed from supernatant fractions of the reaction mixtures, measuring the radioactivity of the immune complexes or the supernatant fractions, and quantitatively determining the amount of such connective tissue protein in the samples with a standard curve constructed with known amounts of radioactively-labelled connective tissue protein of the same type as that released in the organ or tissue affected by such disease.

42. The method for immunochemically detecting or following the pathogenesis of a disease in accordance with any one of claims 37–41 in which the disease is liver fibrosis or cirrhosis, the samples are serum samples and the connective tissue protein is Type I, III or IV collagen.

43. The method for immunochemically detecting or following the pathogenesis of a disease in accordance with any one of claims 37–41 in which the disease is scleroderma, the samples are serum samples and the connective tissue protein is Type I, III or IV collagen.

44. The method for immunochemically detecting or following the pathogenesis of a disease in accordance with any one of claims 37–41 in which the disease is rheumatoid arthritis in the inflammatory-proliferative phase, the samples are synovial fluid samples and the connective tissue protein is Type I, II, III, IV or V collagen.

45. A method for immunochemically detecting or following the pathogenesis of a disease in a human patient suspected or known to have such disease, comprising:
   (a) reacting a first histological or cytological sample taken from such patient with a soluble monoclonal antibody specific for a connective tissue protein which is releasaed in an organ or tissue affected by such disease and is present in such sample;
   (b) allowing such antibodies and connective tissue protein to interact to form antigen-antibody complexes in such histological or cytological sample;
   (c) detecting the antigen-antibody complexes formed in such histological or cytological sample;
   (d) repeating each of such steps on a second, control sample which is known to reflect a non-pathological condition or a particular pathological condition in human beings; and
   (e) comparing the connective tissue protein in such first and second histological or cytological samples to determine whether such connective tissue protein in such first sample reflects a presence or progression of such disease, thereby detecting or following the pathogenesis of such disease in such patient.

46. The method for immunochemically detecting or following the pathogenesis of a disease in accordance with claim 45 in which the antigen-antibody complexes formed in each of the first and second histological or cytological samples are detected by the use of a labelled anti-immunoglobulin.

47. The method for immunochemically detecting or following the pathogenesis of a disease in accordance with claim 46 in which the antigen-antibody complexes formed in each of the first and second histological or cytological samples are detected by
   (a) layering onto such samples containing such antigen-antibody complexes a preparation of anti-immunoglobulin labelled by conjugation to a fluorescent compound;
   (b) allowing such anti-immunoglobulin to form immune complexes with the antigen-antibody complexes; and
   (c) detecting the presence of such connective tissue protein by observing the fluorescence of such anti-immunoglobulin-antigen-antibody complexes by fluorescent light microscopy.

48. The method for immunochemically detecting or following the pathogenesis of a disease in accordance with any one of claims 45–47 in which the disease is atherosclerosis, the histological samples are blood vessel tissue samples and the connective tissue protein is Type I, III, IV or V collagen.

49. The method for immunochemically detecting or following the pathogenesis of a disease in accordance with any one of claims 45–47 in which the disease is cervical and/or uterine cancer, the cytological samples are Pap smears and the connective tissue protein is Type IV collagen.

50. The method for immunochemically detecting or following the pathogenesis of a disease in accordance with any one of claims 45–47 in which the disease is liver fibrosis or cirrhosis, the samples are histological samples and the connective tissue protein is Type I, III or IV collagen.

51. The method for immunochemically detecting or following the pathogenesis of a disease in accordance with any one of claims 45–47 in which the disease is scleroderma, the samples are histological samples and the connective tissue protein is Type I, III or IV collagen.

52. The method for immunochemically detecting or following the pathogenesis of a disease in accordance with any one of claims 45–47 in which the disease in rheumatoid arthritis in the inflammatory-proliferative phase, the samples are histological samples and the connective tissue protein is Type I, III, IV or V collagen.

53. The method for immunochemically detecting or following the pathogenesis of a disease in accordance with any one of claims 45–47 in which the disease is osteosarcoma, the samples are histological samples and the connective tissue protein is Type I collagen.

54. The method for immunochemically detecting or following the pathogenesis of a disease in accordance with any one of claims 45–47 in which the disease is chondrosarcoma, the samples are histological samples and the connective tissue protein is Type II collagen.

55. The method for immunochemically detecting or following the pathogenesis of a disease in accordance with any one of claims 45–47 in which the disease is breast carcinoma the samples are histological samples and the connective tissue protein is Type IV collagen.

56. The method for immunochemically detecting or following the pathogenesis of a disease in accordance with any one of claims 37–41 in which the disease is atherosclerosis, the samples are serum samples and the connective tissue protein is Type I, III, IV or V collagen.

57. The method for immunochemically detecting or following the pathogenesis of a disease in accordance with any one of claims 37–41 in which the disease is osteosarcoma, the samples are serum samples and the connective tissue protein is Type I collagen.

58. The method for immunochemically detecting or following the pathogenesis of a disease in accordance with any one of claims 37–41 in which the disease is chondrosarcoma, the samples are serum samples and the connective tissue protein is Type II collagen.

59. The method for immunochemically detecting or following the pathogenesis of a disease in accordance with any one of claims 37–41 in which the disease is breast carcinoma, the samples are serum samples and the connective tissue protein is Type IV collagen.

60. The method for immunochemically detecting or following the pathogenesis of a disease in accordance with any one of claims 37–41 in which the disease is bone marrow cancer, the samples are serum samples and the connective tissue protein is elastase or Type III collagen peptide.

* * * * *